United States Patent [19]

Porat et al.

[11] Patent Number: 4,757,730
[45] Date of Patent: Jul. 19, 1988

[54] DEVICE FOR RELEASING CONICAL CONNECTORS

[76] Inventors: Amir Porat, 22 Rachvat Eilan St. Givat Shaul, Ramat Filan; Michael Porat, 52 HaMitnadev St., Tel Aviv, both of Israel

[21] Appl. No.: 864,403

[22] Filed: May 19, 1986

[30] Foreign Application Priority Data

Jun. 19, 1985 [IL] Israel ........................................ 75561

[51] Int. Cl.⁴ ........................... B25B 7/02; B25B 27/02
[52] U.S. Cl. ...................................... 81/426.5; 81/485; 29/280; 29/253
[58] Field of Search ................... 81/418–420, 81/424.5, 426.5, 186, 485; 29/278, 280, 282, 234, 253; 254/24; 128/321

[56] References Cited

U.S. PATENT DOCUMENTS

| 319,775 | 6/1885 | Barney | 81/426.5 X |
| 1,462,202 | 7/1923 | Hopper | 128/321 |
| 2,489,842 | 11/1949 | Wochner | 81/124.5 X |
| 4,084,457 | 4/1978 | Berg | 81/424.5 |
| 4,165,745 | 8/1979 | Heifetz | |

FOREIGN PATENT DOCUMENTS

| 0136392 | 4/1985 | European Pat. Off. | |
| 1503106 | 10/1962 | Fed. Rep. of Germany | |
| 1925321 | 5/1969 | Fed. Rep. of Germany | |
| 2025868 | 12/1971 | Fed. Rep. of Germany | |
| 2147183 | 4/1973 | Fed. Rep. of Germany | |
| 3223513 | 6/1982 | Fed. Rep. of Germany | |
| 396253 | 4/1909 | France | 128/321 |

Primary Examiner—Debra S. Meislin
Attorney, Agent, or Firm—Dennison, Meserole, Pollack & Scheiner

[57] ABSTRACT

A device for releasing conical coupling connections including a handle including opposing jaws which define wedge-shaped cross-sections. Preferably, the jaws define a central semi-circular portion adapted to engage the circumference of the conical connector and defining a cross-section of a truncated cone. The handle may include a scissor-like body or a unitary U-shaped body.

2 Claims, 1 Drawing Sheet

U.S. Patent
Jul. 19, 1988
4,757,730
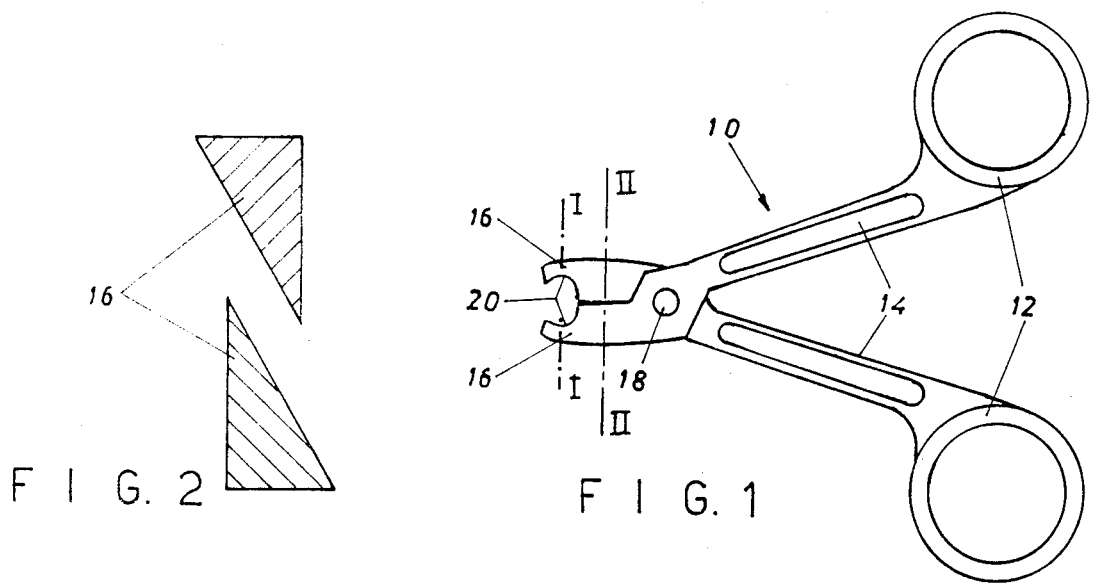
FIG. 2
FIG. 1
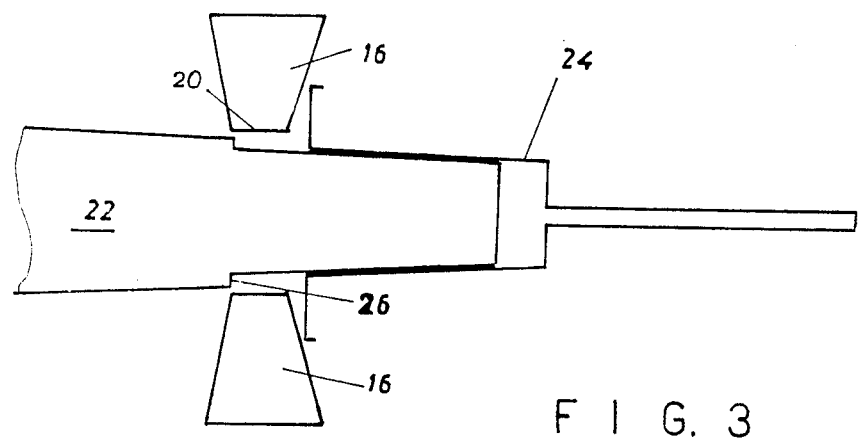
FIG. 3
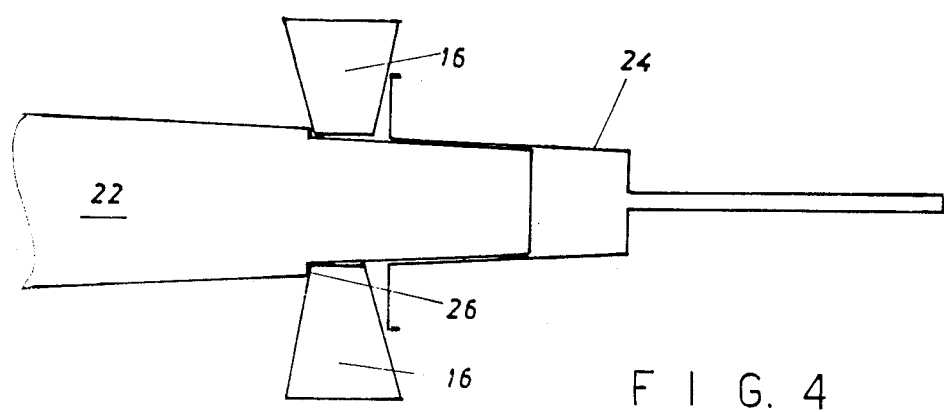
FIG. 4

DEVICE FOR RELEASING CONICAL CONNECTORS

FIELD OF THE INVENTION

The present invention relates to a Luer-type conical connector releasing device, in general, and to apparatus for releasing intravenous, syringe and other Luer type tapered couplings, in particular.

BACKGROUND OF THE INVENTION

There are many applications in medical practice where a conical connector or adapter having a 6% taper (Luer type) is employed. These include coupling of tubing from intravenous fluid to the needle inserted in the vein of the patient, as well as the fitting of an hypodermic needle onto the pointed nozzle of a syringe.

The Luer type adapter is a cone shaped element of a standard taper angle, generally including a raised shoulder partway along its length. The overall length of the conical connector is 7.5 mm minimum. The complete connector includes two portions, one male and one female, frictionally coupled to one another. In practice, it is very difficult to grasp the two portions of the connector and disconect one from the other since the 6% taper angle permits a strong connection between the two. It is particularly difficult when one of the portions defines the base of an hypodermic needle in the vein of a patient from which the connector and attached tubing must be removed, for example, when introducing new infusion material. A similar difficulty is often encountered when removing an hypodermic needle from the nozzle of a syringe.

At present, there are known two methods of coupling and separating conical connectors of the Luer type from a needle. The first is a friction coupling described above wherein the outer surface of the male portion of the conical connector or of the syringe nozzle frictionally engages the inner surface of the base of the needle. Disengagement is accomplished manually by pulling one part from the other.

There is also known a device known as a Luer Lock which includes a threaded coupling which is screwed on and off the needle by rotation and to which the Luer type connector can be coupled. This device can be inconvenient in use since it requires twisting of the fluid tubing with the Luer Lock when being removed from the needle.

SUMMARY OF THE INVENTION

It is an object of the present invention to provide a simple conical coupling releaser for separating two elements joined by a frictional Luer type or other conical connection without requiring twisting or turning of the elements to be separated.

There is thus provided in accordance with the present invention a device for releasing conical coupling connections including handle means including opposing jaws which define wedge-shaped cross-sections.

According to a preferred embodiment of the invention, the handle means include a scissor-like body. According to an alternate embodiment, the handle means include a unitary U-shaped body.

Further according to a preferred embodiment, the jaws define a central semi-circular portion adapted to engage the circumference of the conical connector and defining a cross-section of a truncated cone.

Still further according to a preferred embodiment, the jaws are arranged for sliding motion adjacent one another upon closing of the handle means.

BRIEF DESCRIPTION OF THE DRAWINGS

The apparatus of the present invention will be further understood from the following detailed description taken in conjunction with the drawings in which:

FIG. 1 is a plan view of a conical connector releasing device constructed and operative in accordance with an embodiment of the present invention;

FIG. 2 is a sectional illustration of the jaws of the releasing device of FIG. 1 taken along line II—II;

FIG. 3 is a sectional view taken along line I—I of FIG. 1 of a conical connector releaser according to the present invention engaged about a conical connection before release thereof; and FIG. 4 is a sectional view of the releaser of FIG. 3 after release.

DETAILED DESCRIPTION OF THE INVENTION

There is shown in FIG. 1 a device for releasing a conical connector, most particularly for releasing a 6% taper (Luer type) connection constructed and operative in accordance with an embodiment of the present invention and comprising a handle means 10. As illustrated in FIG. 1, handle 10 comprises a body of scissor-like shape including grippers 12, shanks 14 and jaws 16, the two parts being coupled in any conventional manner, as by pivot pin 18. Grippers 12 may be of any conventional shape, i.e., finger holes as illustrated in FIG. 1, or straight grippers. Alternatively, handle 10 may comprise any other handle means permitting selectable movement of jaws 16, such as a unitary U-shaped body defining jaws 16 at the ends of the U.

Each of jaws 16 defines a generally wedge-shaped or triangular cross-section and the jaws are coupled to one another in such a way that, upon closing the releaser device, the jaws slide adjacent one another in overlapping relationship. One example of suitable jaw cross-section is illustrated in FIG. 2, although any other cross-section permitting overlapping closure can altrnatively be employed.

Each of jaws 16 preferably defines a semi-circular groove 20 in registration with the opposing groove. Groove 20 preferably has a radius approximately equal to or somewhat greater than the radius of the conical connector to be released so as to accomodate the connector and prevent damage thereto during release. It will be appreciated that the cross-section of jaw 16 through semi-circular groove 20 will define a truncated cone.

The method of operation of the conical releaser of the present invention is illustrated in FIGS. 3 and 4, by way of example, during the release of a conventional Luer type 6% taper conical adapter 22 from an hypodermic needle 24. Luer adapter 22 defines a shoulder 26 part way along its length. Needle 24 is frictionally engaged by the tip of the Luer adapter.

To release the Luer adapter, body 10 is opened and the jaws 16 placed around the Luer adjacent the flange of needle 24 and shoulder 26. As the Luer releaser is closed, jaws 16 move closer to the periphery of the Luer connector, the interengagement of the conical sides of the jaws effects a lateral displacement of the jaw elements into engagement with the connector components thus forcing the needle away from the Luer adapter. It will be appreciated that release of a needle from a syringe nozzle, or the release of any other conical connection of virtually any taper angle, will be substantially identical to that described with reference to FIGS. 3 and 4, the jaws being inserted between the flange means of the respective elements to be separated.

It is a particular feature of the present invention that the jaws are coupled so as to close in overlapping relationship. This angling of the jaws permits their insertion into the gap between the needle and the Luer adapter shoulder (or the end wall of the syringe, etc.), and the consequent closure of the jaw forces the elements away from one another.

The device of the present invention is preferably formed of a reinforced plastic material, graphite or plastic fibres, or metal, or can alternatively be formed of any suitable material which will not damage the elements to be separated.

It will be appreciated by those skilled in the art that the invention is not limited to what has been shown and described hereinabove by way of example. Rather, the scope of the invention is limited solely by the claims which follow.

We claim:

1. A tool for separating assembled conical connectors comprising pivoted handle means moveable between open and closed positions and including opposing jaw portions, each jaw further including a semi-circular recess dimensioned to encircle the periphery of one of the conical connectors to be separated, each jaw further including a substantially complementary wedge-shaped cross-sectional portion configured to slidingly engage the other upon manipulation of said handle means and move said jaws laterally away from each other when said handle means is moved to said closed position.

2. A releasing device according to claim 1 and wherein said handle means comprises a scissor-shaped body.

* * * * *